United States Patent [19]
Pound

[11] Patent Number: 6,121,318
[45] Date of Patent: Sep. 19, 2000

[54] MITE AND TICK CONTROL FOR REPTILES

[76] Inventor: Roberl Pound, 59-A Split Rock Rd., Mahopac, N.Y. 10541

[21] Appl. No.: 09/137,981

[22] Filed: Aug. 21, 1998

[51] Int. Cl.$^7$ .......................... A01N 53/00; A61K 31/215
[52] U.S. Cl. ............................................... 514/531
[58] Field of Search .............................................. 514/531

[56] References Cited

U.S. PATENT DOCUMENTS

| | | | |
|---|---|---|---|
| 3,370,571 | 2/1968 | Knapp | 119/159 |
| 3,944,662 | 3/1976 | Miller, Jr. et al. | 424/78 |
| 4,579,085 | 4/1986 | McGuire | 119/156 |
| 4,674,445 | 6/1987 | Cannelongo | 119/156 |
| 5,074,252 | 12/1991 | Morgan | 424/195.1 |
| 5,465,685 | 11/1995 | Dotolo et al. | 119/159 |
| 5,492,693 | 2/1996 | Miller, Jr. | 424/195.1 |

OTHER PUBLICATIONS

The Pyrethroid Insecticides, ICI Plant Protection Division, Taylor & Francis (1985), p. 14.

M. Kaplan, Getting Rid of Reptile Mites, Internet Publication, 11 pages (1997).

Pyrethroids: Their Effects on Aquatic and Terrestrial Ecosystems, National Research Council, Canada, NRCC No. 24376 (1986).

Primary Examiner—Dwayne C. Jones
Attorney, Agent, or Firm—Law Office of Leo Zucker

[57] ABSTRACT

Reptiles are treated to eradicate or to prevent an infestation of ectoparasites, by applying a formulation having a substantially non-volatile active ingredient that is toxic to ectoparasites but generally benign to a reptile to be treated, on an inside surface of a container, and confining the reptile inside the container. In one embodiment, a substrate is placed in the container on which substrate the reptile rests when confined, and the formulation is applied on the substrate. The treatment is particularly suitable for snakes. Permethrin may form the active ingredient of the formulation. The treatment has residual benefits over an extended period of time.

14 Claims, 2 Drawing Sheets

Table 1. (Study 1)

Observed Toxicological Effects caused by Inhalation

| Exposure (seconds) | | OBSERVATION TIME: | | | | | | | | | | | | | | |
|---|---|---|---|---|---|---|---|---|---|---|---|---|---|---|---|---|
| | | 15 min. | 30 min. | 45 min. | 1 hr. | 2 hr. | 3 hr. | 4 hr. | 8 hr. | 12 hr. | 16 hr. | 20 hrs. | 24 hrs. | 32 hrs. | 40 hrs. | 48 hrs. |
| 0 | Group A1 | NOE | NOE | NOE | NOE | NOE | NOE | NOE | NOE | NOE | NOE | NOE | NOE | NOE | NOE | NOE |
| 1 | Group A2 | NOE | NOE | NOE | NOE | NOE | NOE | NOE | NOE | NOE | NOE | NOE | NOE | NOE | NOE | NOE |
| 2 | Group A3 | NOE | NOE | NOE | NOE | NOE | NOE | S | S | S | S | S | S | NOE | NOE | NOE |
| 3 | Group A4 | NOE | NOE | NOE | NOE | S | S | S | S | M | M | M | M | S | S | S |
| 4 | Group A5 | NOE | NOE | NOE | S | M | M | M | SV | SV | SV | SV | M | S | S | X |
| 5 | Group A6 | NOE | NOE | NOE | M | M | M | SV | SV | SV | SV | SV | SV | SV | M | |
| 6 | Group A7 | NOE | NOE | NOE | M | SV | SV | SV | SV | SV | SV | SV | X | | | |
| 0 | Group B1 | NOE | NOE | NOE | NOE | NOE | NOE | NOE | NOE | NOE | NOE | NOE | NOE | NOE | NOE | NOE |
| 1 | Group B2 | NOE | NOE | NOE | NOE | S | S | S | NOE | NOE | NOE | NOE | NOE | NOE | NOE | NOE |
| 2 | Group B3 | NOE | NOE | NOE | NOE | S | S | M | M | S | S | M | M | NOE | NOE | NOE |
| 3 | Group B4 | NOE | NOE | NOE | S | M | M | SV | M | M | M | M | M | M | S | S |
| 4 | Group B5 | NOE | NOE | NOE | M | M | M | SV | SV | SV | SV | SV | SV | SV | X | |
| 5 | Group B6 | NOE | NOE | S | M | SV | SV | SV | SV | SV | SV | SV | X | | | |
| 6 | Group B7 | NOE | NOE | S | | SV | SV | SV | SV | SV | SV | | X | | | |

NOE - No Observable Effect
S - Slight Tremors
M - Moderate Neurological Dysfunction
SV - Severe Neurological Dysfunction
X - Death

FIG. 2

MITE AND TICK CONTROL FOR REPTILES

BACKGROUND OF THE INVENTION

1. Field of the Invention

This invention relates to methods of controlling disease-carrying ectoparasites on animals. In particular, the invention concerns a treatment for reptiles, including snakes, that eradicates and prevents mite and tick infestations.

2. Discussion of the Known Art

Because most insecticides are toxic if applied to or inhaled by domestic animals including reptiles, known treatments for animal pests and parasites apply insecticides where the parasites tend to congregate, instead of directly on or near the animal. Care must be taken to avoid prolonged exposure by the animal to such chemicals, for example, by ensuring that the chemicals evaporate quickly when used, and that they have a relatively short residual effect.

U.S. Pat. No. 3,370,571 (Feb. 27, 1968) discloses apparatus for spraying livestock to control flying insect pests. The apparatus operates to apply pesticides using an aqueous solution that evaporates or drains off quickly. Pesticides suited for application using the apparatus of the '571 patent may be fatal to reptiles, however, since aqueous solutions are absorbed through reptile skin and the vapors would likely be inhaled. This can result in various health problems, or death of the reptile.

Ectoparasites found on reptiles, particularly snake mites, require a pesticide having long-term residual action to kill any eggs that may hatch out over a period of several weeks. Thus, the pesticide cannot be water soluble since most reptile enclosures require a high humidity environment, and a water soluble pesticide would break down or wash away under such conditions.

U.S. Pat. No. 5,492,693 (Feb. 20, 1996) describes a composition of sea salt and water for treating pet animals and surfaces infested with ectoparasites. The composition may also include a skin conditioner. But sea salts are potentially harmful to reptiles whose physiology and tolerance to various chemicals differ from those of common pets. Skin conditioners disclosed by the '693 patent may also be harmful to reptiles if the animal is emerged or soaked in them.

See also, U.S. Pat. No. 4,579,085 (Apr. 1, 1986) which discloses a synthetic resin strip for attachment to, e.g., the ear of an animal, and U.S. Pat. Nos. 4,674,445 (Jun. 23, 1987) and 5,074,252 (Dec. 24, 1991).

SUMMARY OF THE INVENTION

A method is provided for treating a reptile to eradicate or to prevent an infestation of ectoparasites, wherein the treatment has residual properties without inflicting harm to the reptile.

According to the invention, a method of treating a reptile to eradicate or to prevent an infestation of ectoparasites, includes applying a formulation having a substantially non-volatile active ingredient that is toxic to ectoparasites but generally benign to the reptile, on an inside surface of a container, and confining the reptile inside the container.

According to another aspect of the invention, a method of treating a reptile to eradicate or to prevent an infestation of ectoparasites, placing a substrate in an container on which substrate a reptile to be treated will rest when confined in the container, and applying a formulation having a substantially non-volatile active ingredient that is toxic to ectoparasites but generally benign to the reptile, on the substrate, and confining the reptile inside the container.

According to another aspect of the invention, a method of treating a snake to eradicate an infestation of ectoparasites, includes applying a formulation having Permethrin as an active ingredient on the snake.

For a better understanding of the invention, reference is made to the following description taken in conjunction with the accompanying drawing and the appended claims.

BRIEF DESCRIPTION OF THE DRAWING

In the drawing:

FIG. 2 is a table showing observed toxicological effects of a formulation having permethrin as an active ingredient on defined groups of snakes.

DETAILED DESCRIPTION OF THE INVENTION

Figure 1:
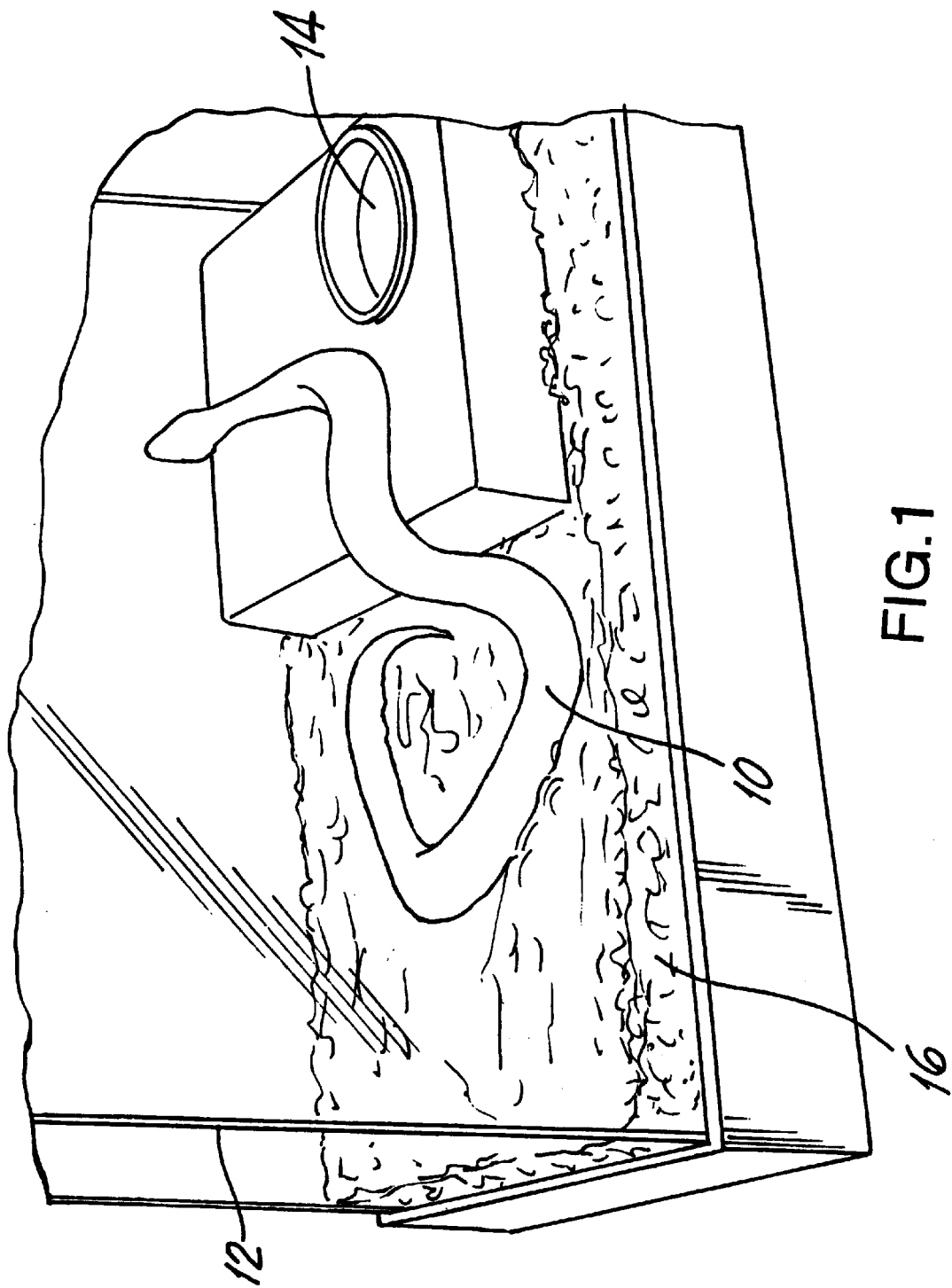
FIG. 1 shows a pet snake confined in a cage, with substrate material on a floor of the cage.

FIG. 1 shows a pet snake 10 in a glass enclosure 12. The snake is provided with a dish 14 of fresh drinking water. A bedding or substrate 16 of material such as aspen mulch is placed on the floor of the enclosure 12, to provide a suitable environment for the snake 10.

It has been discovered that a chemical formulation including Permethrin as an active ingredient works effectively to protect snakes and other reptiles from disease-carrying mites and ticks. Permethrin is currently available from FMC Corporation, Philadelphia, Pa., and is the common chemical name for (3-phenoxyphenyl) methyl (+/−) cis/trans 3-(2,2-dichloroethenyl) 2,2-dimethylcyclopropanecarboxylate. In treatment methods described below, the reptile and its water supply are removed from the animal's container or cage, and the formulation is applied either on a surface inside the cage or to a substrate on the cage floor, at a rate of about 1 to 2 seconds per square foot. The cage is then ventilated for about five minutes, and the reptile is replaced. This method avoids a direct application of the formulation directly on the reptile's skin. In cases of persistent ectoparasites, a towelette is soaked with the formulation and a portion of the reptile's back is rubbed with the moist towelette, also as described below. It has been found that unlike other insecticides most of which are fatal or toxic to reptiles, Permethrin is non-toxic to reptiles when used as described herein. The results are unexpected in view of the fact that Permethrin is a so-called pyrethroid, and other pyrethroids such as Pyrethrin are generally toxic to reptiles.

Experiments were performed to determine the effectiveness of a formulation using Permethrin as an active ingredient to eradicate mites, ticks and other ectoparisites that commonly feed on reptiles. Three studies were conducted to evaluate the efficacy and potential toxicity that various methods of application would have on the ectoparasites, and on the host being treated.

EXAMPLE 1

A total of 140 snakes were separated into two groups of 70, of which 20 snakes were maintained as control subjects. All test snakes were purposely infested with snake mites (Ophionyssus natricis) one week before testing commenced. The 140 snakes were divided into two groups. Group A snakes were kept in containers containing aspen mulch as a substrate. Group B snakes were kept in bare containers.

Each group was further divided into seven groups of ten snakes, namely, Groups A-1 through A-7 and Groups B-1 through B-7. Each sub-group of ten snakes contained two neonate snakes of the same species for a total of five species tested in each subgroup. These five species were duplicated for every subgroup in both Group A and Group B, resulting in a total of 28 neonate snakes of each species being tested.

Containers used to hold snakes during test were ¼-lb "deli cups" which were clear plastic containers having no ventilation holes and with tight-fitting lids. As mentioned, a ½-inch deep layer of aspen mulch was placed in each of the Group A containers as a supporting bed for the reptile, while the inside surfaces of the Group B containers remained bare.

The five species of snakes selected for experiment were as follows:

| | |
|---|---|
| Brazilian Rainbow Boa | (Epicrates cenchria cenchria) |
| Sonora Gopher Snake | (Pituophis melanoleucus affinis) |
| Western Hognose Snake | (Heterodon nasicus) |
| Common Boa | (Boa constrictor constrictor) |
| Common Garter Snake | (Thamnophis sirtalis sirtalis) |

Snakes were maintained at a temperature of 85 degrees F. during the treatment and observation period. No food or water was introduced into the containers during an application treatment and for up to 48 hours after the treatment, as explained below.

METHODOLOGY

The 70 containers in subgroups A-1 through A-7 were prepared as described. Two snakes from each species were placed into the containers and then secured using the lids. Subgroups B-1 through B-7 were prepared in the same manner.

Subgroups A-1 and B-1 were placed in another location to be used as controls. Subgroups A-2 through A-7 and subgroups B-2 through B-7, were treated with the present formulation as follows:

The lid was removed from each container. A formulation comprising about 0.5 percent by volume of Permethrin was sprayed directly on the subject reptile and inside the corresponding container (on the substrate for Group A; on the bare floor for Group B) for a period of time indicated. The lid was then securely placed back on the container. The subgroups were sprayed as follows:

Subgroups A-2 and B-2; 1 second spray time
Subgroups A-3 and B-3; 2 seconds
Subgroups A-4 and B-4; 3 seconds
Subgroups A-5 and B-5; 4 seconds
Subgroups A-6 and B-6; 5 seconds
Subgroups A-7 and B-7; 6 seconds Once treated, the test subjects of the above subgroups were observed over a 48-hour period according to the Table in FIG. 2 for any evidence of neurological toxicity or any other behavioral abnormalities. At the completion of the observation period, there were no living mites or any evidence of mite activity on the test snakes.

After completion of the 48-hour observation period, mites were introduced into the containers once a week over a 30-day period of time. The snakes were fed once a week and provided with drinking water daily. All introduced mites died within 15 minutes of being exposed to the treated surfaces during this 30-day period. Moreover, there was no evidence of the snakes becoming reinfested.

EXAMPLE 2

A total of 20 snakes, ten per Group A and ten per Group B were placed in containers using the same protocols as in Example 1. In this study, the formulation of Example 1 was applied directly to the snakes by means of a saturated cloth, rather than by spraying. Snakes were removed from their containers, wiped one time from behind the head to the vent with a cloth treated with the formulation, and then placed back into the container and covered with the container lid.

The snakes were observed at the same intervals as were followed in Example 1. There were no observable effects recorded for any of the subject animals. Further, there were no living mites or any evidence of mite activity on test snakes at the completion of the observation period.

EXAMPLE 3

A ½-inch layer of aspen mulch substrate was placed in a first group of ten containers, and then sprayed with the formulation of Example 1 for a period of six seconds. The containers were then allowed to ventilate and dry for five minutes. Two snakes from each of the five listed species were then placed into the containers, and covered with the container lids.

A second group of ten containers were left bare and were treated in the same manner as above. Two snakes of each species were placed into the containers and secured with lids.

The snakes were observed using the same intervals as in Example 1, above. There were no observable effects recorded for any of the subject animals. Further, there were no living mites or any evidence of mite activity on the snakes at the completion of the observation period.

After completion of the 48-hour observation period, mites were introduced into the containers once a week over a 30 day period of time. Snakes were fed once a week and provided with drinking water daily. All introduced mites died within 15 minutes of exposure to the treated surfaces. Further, there was no evidence of the snakes becoming reinfested.

CONCLUSION

In all three Examples, the formulation of Example 1 was completely effective in eradicating all mites present on the test snakes. In Example 1, snakes treated for three or more seconds did exhibit neurological dysfunction to various degrees which in most cases resulted in the death of the snake within 48 hours. In Examples 2 and 3, there were no observable effects recorded for any of the snakes tested.

Results of Examples 2 and 3 show that the formulation of Example 1 was not toxic to the test snakes even when exposed through dermal contact. Allowing the snakes to inhale vapors created by the methodology used in Example 1 resulted in neurological dysfunction, however. One possible explanation is that a physiological process called ester-hydrolysis breaks down various pyrethroids into non-toxic by-products when absorbed through the skin. Inhalation of an aerosol spray might serve to bypass such a process allowing toxic levels of pyrethroids to be absorbed into the reptile's system.

The foregoing demonstrates a safe and effective treatment to control ectoparisites on reptiles, particularly snakes. In the disclosed Examples, a formulation including Permethrin as an active ingredient is applied on a surface inside the reptile's cage or on a substrate in the cage, or the formulation is wiped directly on the reptile's skin using a cloth or towelette.

The disclosed treatment can render any type of substrate (e.g., aspen mulch, newspaper, wood chips, orchard bark, crushed walnut shells, sand or dirt), or even a bare floor of a reptile's enclosure, "miteproof" for a period of up to 30 days. The treatment eliminates active infestations, and ones resulting from hatching of any eggs during that period once hatching larval mites contact the treated surface or substrate.

While the foregoing description represents a preferred embodiment of the invention, it will be obvious to those skilled in the art that various changes and modifications may be made, without departing from the spirit and scope of the invention pointed out by the following claims.

I claim:

1. A method of treating a reptile to eradicate or to prevent an infestation of ectoparasites, comprising:

applying a formulation having a substantially non-volatile active ingredient of not more than about 0.50 percent permethrin on an inside surface of a reptile cage; and confining a reptile to be treated for prevention or eradication of ectoparasites inside the reptile cage.

2. The method of claim 1, including applying the formulation directly on the reptile.

3. The method of claim 2, wherein the formulation is applied on the reptile by wiping with a cloth or towelette moistened with the formulation.

4. The method of claim 2, wherein the formulation is applied on the reptile by spraying.

5. The method of claim 4, including carrying out the spraying step for not more than about two seconds.

6. A method of treating a reptile to eradicate or to prevent an infestation of ectoparasites, comprising:

placing a substrate in a reptile cage on which substrate a reptile to be treated for prevention or eradication of ectoparasites rests when the reptile is confined in the cage;

applying the formulation having a substantially non-volatile active ingredient of not more than about 0.50 percent permethrin on the substrate; and confining the reptile inside the reptile cage.

7. The method of claim 6, including applying the formulation directly on the reptile.

8. The method of claim 7, wherein the formulation is applied on the reptile by wiping with a cloth or towelette moistened with the formulation.

9. The method of claim 7, wherein the formulation is applied on the reptile by spraying.

10. The method of claim 9, including carrying out the spraying step for not more than about two seconds.

11. A method of treating a reptile to eradicate an infestation of ectoparasites, comprising applying a formulation having a substantially non-volatile active ingredient of not more than about 0.50 percent permethrin directly on the reptile.

12. The method of claim 11, wherein the formulation is applied on the reptile by wiping with a cloth or towelette moistened with the formulation.

13. The method of claim 11, wherein the formulation is applied on the reptile by spraying.

14. The method of claim 13, including carrying out the spraying step for not more than about two seconds.

* * * * *